United States Patent [19]
Balazs et al.

[11] Patent Number: 5,128,326
[45] Date of Patent: * Jul. 7, 1992

[54] DRUG DELIVERY SYSTEMS BASED ON HYALURONANS DERIVATIVES THEREOF AND THEIR SALTS AND METHODS OF PRODUCING SAME

[75] Inventors: Endre A. Balazs, Ft. Lee; Adolf Leshchiner, Fairview; Nancy E. Larsen, Ridgefield Park, all of N.J.

[73] Assignee: Biomatrix, Inc., Ridgefield, N.J.

[ * ] Notice: The portion of the term of this patent subsequent to Apr. 15, 2003 has been disclaimed.

[21] Appl. No.: 559,413

[22] Filed: Jul. 23, 1990

Related U.S. Application Data

[60] Continuation of Ser. No. 320,822, Mar. 9, 1989, abandoned, which is a continuation of Ser. No. 140,877, Jan. 6, 1988, abandoned, which is a continuation of Ser. No. 804,178, Nov. 29, 1985, abandoned, which is a continuation-in-part of Ser. No. 678,895, Dec. 6, 1984, Pat. No. 4,582,865, and a continuation-in-part of Ser. No. 709,977, Mar. 8, 1985, Pat. No. 4,636,524, and a continuation-in-part of Ser. No. 755,976, Jul. 18, 1985, Pat. No. 4,605,691, said Ser. No. 709,977, and Ser. No. 755,976, each is a division of Ser. No. 678,895.

[51] Int. Cl.$^5$ ................. A61K 31/715; A61K 9/70; A61F 13/00
[52] U.S. Cl. ................... 514/54; 424/446; 514/769
[58] Field of Search .............. 514/54, 769; 424/446

[56] References Cited

U.S. PATENT DOCUMENTS

| | | | |
|---|---|---|---|
| 3,357,784 | 12/1967 | Kasper | 8/129 |
| 3,887,703 | 6/1975 | Manoussos et al. | 514/54 |
| 4,141,973 | 2/1979 | Balazs | 536/55.1 |
| 4,303,676 | 12/1981 | Balazs | 424/359 |
| 4,487,865 | 12/1984 | Balazs | 524/29 |
| 4,500,676 | 2/1985 | Balazs | 424/81 |
| 4,582,865 | 4/1986 | Balazs et al. | 524/29 |
| 4,636,524 | 1/1987 | Balazs et al. | 514/781 |

FOREIGN PATENT DOCUMENTS

| | | | |
|---|---|---|---|
| 137297 | 4/1985 | European Pat. Off. | 514/54 |
| 57-185208 | 11/1982 | Japan | 514/54 |
| 769287 | 3/1957 | United Kingdom | 514/54 |

OTHER PUBLICATIONS

Hassan et al., Acta Anaethesiol Scand., 1985, pp. 384–388.

*Primary Examiner*—Ronald W. Griffin
*Attorney, Agent, or Firm*—Sheldon Palmer

[57] ABSTRACT

Disclosed are drug delivery systems based on a polymeric component which is soluble or insoluble (cross-linked) hyaluronan or hyaluronan copolymerized with another hydrophilic polymer or hylan and one or more substances having biological or pharmacological activity and methods of preparing same.

41 Claims, No Drawings

DRUG DELIVERY SYSTEMS BASED ON HYALURONANS DERIVATIVES THEREOF AND THEIR SALTS AND METHODS OF PRODUCING SAME

CROSS REFERENCE TO RELATED APPLICATIONS

This application is a continuation of copending application Ser. No. 07/320,822, filed Mar. 9, 1989, now abandoned, which is a continuation of copending application Ser. No. 07/140,877, filed Jan. 6, 1988, now abandoned, which is a continuation of copending application Ser. No. 06/804,178, filed Nov. 29, 1985, now abandoned, which is a continuation-in-part of copending applications 06/678,895, filed Dec. 6, 1984, now U.S. Pat. No. 4,582,865; and a continuation-in-part of Ser. No. 06/709,977, filed Mar. 8, 1985, now U.S. Pat. No. 4,636,524; and a continuation-in-part of Ser. No. 06/755,976, filed Jul. 18, 1985, now U.S. Pat. No. 4,605,691, the latter two applications being in turn divisions of copending application Ser. No. 06/678,895.

BACKGROUND OF THE INVENTION

1. Field of the Invention

The present invention relates to drug delivery systems based on hyaluronon, derivatives thereof such as hylan and their salts, methods of preparing same as well as uses thereof.

2. The Prior Art

Hyaluronic acid ("HA") is a well known, naturally occurring polysaccharide containing alternating N-acetyl-D-glucosamine and D-glucuronic acid monosaccharide units linked with 1→4 bonds and the disaccharide units linked with 1→3 glycoside bonds. In keeping with generally accepted chemical nomenclature for polysaccharides, the term "hyaluronan" is increasingly being used in place of the traditional "hyaluronic acid". As used herein, hyaluronan is intended to mean hyaluronic acid, salts thereof such as the sodium salt, and chemically modified derivatives of hyaluronan such as "hylan". Strictly speaking, hylan is not hyaluronan; but for purposes of this specification the two terms are used interchangeably because within the context of the invention their use and application are interchangeable. Hylan is a cross-linked, but nevertheless soluble derivative of HA whose preparation is described in detail in copending application Ser. No. 710,929, filed Mar. 12, 1985, now U.S. Pat. No. 4,713,448. Stated briefly, hylan is prepared by subjecting HA to a cross-linking reaction in situ, that is, in the animal tissue from which it is obtained before its extraction from such tissue. It is soluble notwithstanding its cross-linked nature because the degree of cross-linking is relatively low as compared with more traditional cross-linked HA. Hyaluronic acid usually occurs as the sodium salt. The molecular weight of HA is generally within the range of 50,000 to $8 \times 10^6$ and sometimes even higher.

Hyaluronic acid is one of the major components of the extracellular matrix and is found in abundance in some tissues like synovial fluid and the vitreous of the eye. Hyaluronic acid and its salts give very viscous and elastic solutions in water or physiological salt solution.

Being a naturally occurring polymer, hyaluronic acid does not give a foreign body reaction when implanted into a living body and has an excellent biocompatibility. The combination of these properties together with the known viscoelasticity of HA facilitates the use of hyaluronic acid in the biomedical field. Thus, a 1% solution of sodium hyaluronate (Healon®) is used in eye viscosurgery (L. A. Pape and E. A. Balazs, Ophthalmology, 87, No. 7, 1980). Hyaluronic acid is also used to impart biocompatibility to various polymeric materials. (E. A. Balazs and A. Leshchiner, U.S. Pat. No. 4,500,676, 1985).

SUMMARY OF THE INVENTION

Hereinafter, the terms hyaluronic acid and hyaluronan are used interchangeably; that is, the use of either one is intended to include the other and their use is also intended to include hylan.

In one aspect thereof, the present invention provides water-soluble formulations containing hyaluronic acid or its salts and at least one substance having biological or pharmacological activity.

In another aspect, the invention provides cross-linked gels of hyaluronic acid and at least one other hydrophilic polymer copolymerizable therewith and containing at least one substance having biological or pharmacological activity.

In still another aspect, the invention provides methods of preparing the above mentioned products of the invention.

Finally, the invention provides methods of using the products of the invention.

The present invention is directed to drug delivery systems based on hyaluronic acid in soluble or non-soluble cross-linked forms. In both cases, non-modified or modified hyaluronic acid serves as a vehicle which provides a slow release of a drug from a system.

The drug delivery system according to the present invention includes the following:

1. Hyaluronic acid solutions in which a drug substance is dissolved or dispersed;
2. A cross-linked hyaluronic acid gel forming a macromolecular "cage" in which a drug substance is dispersed;
3. A cross-linked mixed gel of hyaluronic acid and at least one other hydrophilic polymer in which a drug substance is dispersed;
4. A cross-linked gel of hyaluronic acid or cross-linked mixed gel of hyaluronic acid and at least one other hydrophilic polymer containing a drug substance which is covalently attached to the macromolecules of hyaluronic acid or the other polymer.

Any substance which has biological or pharmacological activity and which is normally considered to be a drug can be used as the drug component in the products according to the present invention. This substance can be soluble or not soluble in aqueous medium; it can be of relatively low molecular weight or it can be a polymeric drug, and the choice of the substance will clearly depend upon the specific use of the end product. It should be understood that any combination of one or more drug substances can be used in the products according to the invention.

As mentioned above, the polymeric component which imparts the drug delivering properties to the product of the invention is hyaluronan or hylan in various forms which differ in their solubility in aqueous medium as well as combinations of hyaluronic acid with other hydrophilic polymers. We have found that solutions of hyaluronic acid can provide the above mentioned delivering properties. Hyaluronic acid, when in its most highly polymerized form, i.e., with a molecular weight which can exceed $8 \times 10^6$, forms solutions in water or physiological salt solutions which demonstrate outstanding viscoelasticity.

When a drug substance is dissolved or dispersed in this solution, its diffusion is substantially slower and this contributes to the delivering properties of such a system. In the case of a drug containing cationic groups, an ionic interaction can occur between hyaluronic acid macromolecules having carboxyl groups and the drug and this interaction slows down the diffusion of the drug from the system even further.

The hyaluronic acid solutions discussed hereinabove also include a so-called acid putty. (Balazs, A. E., Fed. Proc. Vol. 25, No. 6, 1817–22 (1966)) Hyaluronic acid is known to form a very elastic, almost hard body when the pH of a solution thereof is around 2.5. The hardness of this putty depends mainly upon the hyaluronic acid and sodium chloride concentrations in the solution and the temperature. This putty, despite its consistency, should be considered as a solution because it can be infinitely diluted with water to give dilute solutions with the usual properties of a solution. We have found that the ability of hyaluronic acid to form the acid putty can be conveniently used to obtain a product with drug delivering properties. It should be understood, however, that these products can only be used in certain circumstances because they are quite acidic.

The hyaluronic acid concentration in the products, based on the soluble polymers, can be in the range of from about 0.05 to 4% by wt. and higher, depending on the end use of the product. The drug concentration can be varied over very broad limits and preferably should be chosen depending upon the solubility of the drug, its pharmacological activity, the desirable effect of the end product, etc. Although the above discussed products can be used as injectables, the other products according to the invention containing non-soluble hyaluronic acid are substantially more efficient as injectable drug delivery systems. For this reason, it is preferable to use soluble products for topical applications, i.e., as eye drops or for skin treatment.

We have found that eye drops containing hyaluronic acid remain on the surface of the eye longer and thus provide longer and more uniform action of the drug on the eye.

The other types of drug delivery products according to the invention are based on insoluble cross-linked gels of hyaluronic acid. Numerous substances can be used to cross-link hyaluronic acid including formaldehyde, epoxides, polyaziridyl compounds, divinyl sulfone and others. We have found that the preferred cross-linking agent is divinyl sulfone. This substance reacts readily with hyaluronic acid in aqueous alkaline solutions at room temperature, i.e., about 20° C., thereby providing cross-linked HA gels. These gels swell in water and water containing media. The swelling ratio depends upon the degree of cross-linking of the gel. We have found the degree of cross-linking can be controlled by changing several factors including the molecular weight of the HA, its concentration in the reaction mixture, the alkali concentration and the polymer/DVS ratio. The reaction is very fast and in most cases a strong gel can be obtained within several minutes. The swelling ratio of these gels can be from 20 up to 8000, and more, depending upon the reaction parameters.

It has also been found that the swelling ratio of cross-linked HA gels is substantially greater than the swelling ratio of cross-linked gels of other polysaccharides obtained under the same reaction conditions. This can probably be explained by the unique nature of HA (as compared to other polysaccharides) and its water solutions. We have found that in water, a large molecule of HA forms a very flexible, long random coil which takes up an extremely large volume in the solution. For example, the specific volume of a hydrated HA molecule in a physiological salt solution is about $2-6 \times 10^3$ ml/g. That means that in a quite low concentration water solution of HA, a steric exclusion phenomenon occurs which will substantially affect not only the physicochemical properties of the solution, but the reaction of the HA with low molecular weight substances as well. In other words, the nature of the HA solutions affects the degree of cross-linking and the behavior of the cross-linked gel in a manner quite unlike anything that occurs with other polysaccharides.

We have also found that this unique property of HA to give highly swollen cross-linked gels can be used to great advantage to effect modification of the properties of cross-linked gels made of mixtures of HA with other hydrophilic polymers. These polymers include other polysaccharides, synthetic and natural, such as hydroxyethyl cellulose, carboxymethyl cellulose, xanthan gum, glycosaminoglycans, proteins and glyco proteins of various types, such as collagen, elastin, albumin, globulin, etc, sulfated proteins, synthetic water-soluble polymers, such as polyvinyl alcohol and its co-polymers, co-polymers of poly-(hydroxyethyl) methacrylate and the like. In other words, any polymer soluble in water or aqueous alkaline solutions and containing groups capable of reacting with DVS, namely, hydroxyl, amino or sulfhydryl groups, can be used to obtain highly swollen cross-linked mixed gels of HA.

Another convenient method of obtaining cross-linked hyaluronic acid or mixed hyaluronic acid and other polymer gels comprises treating dry polymer preparations, i.e., in the form of a film with a cross-linking agent and subsequent swelling of the product in the desired medium. Thus, a dry film made of hyaluronic acid or of a mixture of hyaluronic acid with another polymer (or polymers) can be cross-linked by treatment in solution of divinyl sulfone in a mixture of water and a solvent which cannot dissolve hyaluronic acid and which is inert towards the cross-linking agent, e.g., acetone. By changing the ratio between water and the organic solvent, the swelling ratio of the cross-linked film in water can be conveniently controlled. However, the swelling ratios of these cross-linked products are usually substantially less than for gels obtained by cross-linking carried out in solutions of hyaluronic acid or its mixtures with other polymers.

The cross-linked gels according to the present invention can be used as such or in combination with various supports or substrates, such as polymeric porous sponges, gauze, polymeric films, etc.

We have found that the above described gels of hyaluronic acid or mixed gels of hyaluronic acid with other polymers are excellent drug delivery systems when loaded with a substance or substances having pharmacological or biological activity.

The domain of the cross-linked hyaluronic acid (either alone or co-cross-linked with other polyanionic or neutral polymers) forms a so-called "molecular cage". In this cage, hydrophilic or hydrophobic molecules of various pharmacological or biological activity can be dispersed. Thus, the cage constitutes a depot for these substances of various molecular sizes. The substances contained in the domain of the molecular cage will be delivered into the environment by diffusion therefrom. The delivery process is controlled by such factors as the exclusion volume effect and the pore size of the molecular cage and by the molecular interaction between the polymeric network and the substance contained therein. Thus, the molecular cage forms a depot for the controlled delivery of drugs or other substances to the skin or other tissues.

There are several methods for combining a drug with the gel and, accordingly, several types of products which can be obtained.

One of the methods comprises diffusing a drug into a gel when the gel is put into a solution of the drug. The diffusion process is usually slow and depends upon the drug concentration, temperature of the solution, size of the gel particles, etc. The product obtained by this method is a gel in which a drug substance is uniformly dispersed.

The same type of product can be obtained by dehydrating a hyaluronic acid gel and reswelling it in a drug solution. To dehydrate a gel one can use a water-miscible organic solvent or alternatively, water from a gel can be removed by drying. However, we have found that it is preferable to use a solvent because after drying at a low or elevated temperature, the gel cannot reswell to its initial degree of swelling. On the other hand, after dehydrating with a solvent, the gel swells to the same volume it had before the treatment. We have found that preferable solvents are ethanol and isopropanol, and ketones such as acetone, though other solvents can also be used.

Yet another method can be used to obtain products of this type. This method comprises allowing a concentrated hyaluronic acid gel resulting from a cross-linking reaction previously carried out in a relatively concentrated solution of hyaluronic acid to swell in a solution of a drug substance.

Although these three methods all result in products which are essentially the same, each of the methods has certain advantages when compared to any of the other methods for any specific product and, hence, the choice of method should be made with consideration given to such parameters as nature of the drug, the desired concentration of the drug in the system, the delivery rate, etc.

A drug delivery system of another type according to the present invention is one in which a drug is covalently attached to macromolecules of hyaluronic acid and/or other polymers forming a gel. These systems are characterized by a substantially slower rate of delivery than those described above. Delivery of a drug from these systems occurs when the gel is degraded in the living body as a result of numerous metabolic processes taking place in vivo. The degradation process is usually slower than diffusion which provides the delivery of a drug in other types of products according to the present invention. Nevertheless, the rate of the degradation process can be controlled by several means, including adjusting the density of the cross-links in the gel or by co-cross-linking hyaluronic acid with polymers which can be degraded in the body more easily than hyaluronic acid, e.g., proteins. By changing the concentration of such polymer components in the mixed gels, one can conveniently control their rate of degradation and, thus, the rate of drug delivery.

Another possibility of drug delivery for this type of product involves the use of such chemical bonds for attachment of a drug to polymeric molecules forming a gel which have a controllable rate of hydrolysis in a physiological environment.

To obtain this type of a product one can use a drug substance which can react with a cross-linking agent. In this case, the attachment of a drug to polymers occurs in a cross-linking reaction used for the gel formation. Yet another method can be used to obtain this product. This method comprises chemically modifying a cross-linked gel after its formation, using the reactive hydroxyl groups of hyaluronic acid or the reactive groups of the polymers co-cross-linked with the hyaluronic acid to which a drug substance can be attached by numerous chemical reactions. Alternatively, additional reactive groups can be introduced by chemical treatment of a cross-linked gel which affects the macromolecules of hyaluronic acid or co-cross-linked polymers and a drug can be covalently attached to these newly formed reactive groups.

The drug delivery products according to the present invention can be used for any application where conventional drugs are used—in topical formulations for use in ophthalmology and dermatology, as injectable or implantable materials, etc. The principal advantage of these products is provided by the fact that the polymeric component of the product, namely, hyaluronic acid in soluble or insoluble form, has outstanding biocompatibility and does not cause any complications when used in humans. By being combined with other materials like polymeric substrates, sponges, gauze, etc., the drug delivery products according to the invention can be used in numerous medical devices including contraceptive devices, wound dressings, drug delivery patches, etc.

DESCRIPTION OF THE PREFERRED EMBODIMENT

The processes by which the hereinabove described products are obtained will now be described in detail.

In order to obtain a hyaluronic acid solution in which a drug substance is dissolved or dispersed any conventional method can be used. Sodium hyaluronate or hyaluronic acid from any source can be dissolved in water or in physiological saline to a desired concentration and then a drug is dissolved or dispersed in the resulting solution. Alternatively, a solution or dispersion of a drug can be mixed with hyaluronic acid solution. The polymer concentration is chosen depending upon the end use of the product and the molecular weight of hyaluronic acid. We have found that it is preferable to use a high molecular weight polymer, i.e., a hyaluronic acid with a molecular weight of $1 \times 10^6$ or higher. The usable concentration of hyaluronic acid of this molecular weight can vary from as low as 0.05 wt. % for ophthalmic solutions to as high as 2 wt % and even higher for skin formulations. The drug concentration is chosen depending upon the desired activity of the product.

As mentioned above, the preferred cross-linking agent for obtaining cross-linked gels is divinyl sulfone. In order to obtain a cross-linked gel, a sample of sodium hyaluronate or hyaluronic acid from any source is dissolved in dilute alkaline solution. The molecular weight of HA can be from 50,000 up to $8 \times 10^6$ and even higher. The molecular weight affects the reaction—the higher the molecular weight the greater the possibility of obtaining a cross-linked gel.

The alkali concentration in the reaction mixture can be from 0.005M to 0.5M and higher. The lower limit is dictated by the necessity to have the pH of the medium not lower than 9 and the upper limit by the hydrolysis of HA in an alkaline solution. Usually, a decrease in alkali concentration results in gels with a greater swelling ratio, probably because a smaller amount of DVS takes part in the cross-linking reaction.

The concentration of HA in the starting solution can vary from 1% by weight up to 8% by weight and higher. When the concentration is below the lower limit, a cross-linked gel cannot be obtained even at a low HA/DVS ratio. When the concentration is too high, the solution becomes so viscous that it is difficult to handle it. The HA concentration substantially affects the swelling behavior of the gels: the swelling ratio usually decreases with HA concentration.

We have found that the HA/DVS ratio in the reaction mixture is another parameter which can be conveniently used to control the swelling ratio of the cross-linked HA gel. An increase in the ratio results in more highly swollen soft gels (the swelling ratio is about 4000 and higher), whereas hard and less swollen gels are obtained when this ratio is decreased. In general, the HA/DVS weight ratio can be from 15:1 to 1:5 and lower.

The cross-linking reaction is usually carried out at room temperature, i.e., about 20° C., but it can be performed at a lower or higher temperature, if desired. However, it should be kept in mind that HA degrades relatively rapidly in alkaline solutions at elevated temperatures and, if such degradation occurs, the decrease in MW can affect the properties of the obtained gels.

The cross-linking reaction is relatively fast and strong gels are formed usually in several minutes when the HA concentration is high enough and the HA/DVS ratio is low. But even at low HA concentration in the reaction mixture, the gel formation starts usually 10-15 minutes after addition of DVS. We have found that in most cases one hour is sufficient for completion of the cross-linking reaction.

To obtain mixed cross-linked gels of hyaluronic acid and other hydrophilic polymers, the same reaction conditions as for HA alone can be used. The swelling ratio of these gels can be conveniently controlled by varying the HA content in the polymer mixture. The swelling ratio is usually increased with an increase of the HA content. The composition of the polymer mixture in a mixed gel can vary over a broad range depending on the swelling ratio of the cross-linked gel, biodegradability, rate of drug delivery desired, etc. The preferred content of hyaluronic acid in the mixture is from 5 to 95 wt. %. The choice of a polymer or polymers to be co-cross-linked with hyaluronic acid depends upon many factors as has already been discussed above.

To load a cross-linked swollen gel with a drug using the diffusion process, the gel can be put into a drug solution. The time for completion of this process depends upon gel particle size, gel swelling ratio, temperature of the process, stirring, concentration of the drug in the solution, etc. By proper combination of these parameters, a swollen gel can be loaded with a drug in a relatively short period of time.

We have found that good results can be obtained when a gel obtained after a cross-linking reaction is allowed to swell in a drug solution. The excess alkali which is present in the gel can be neutralized with hydrochloric acid with the formation of sodium chloride, a substance which is desirable, or at least not undesirable, in many drug delivery products.

To dehydrate a cross-linked gel with a solvent it is enough to put the gel, in any form, i.e., as fine particles or as a membrane, into a solvent, preferable a volatile solvent, e.g., isopropanol, and keep it in the solvent for a sufficient amount of time to remove water from the gel. The degree of water removal depends upon the size of the particles or the membrane thickness, the gel/solvent ratio, etc. The treatment with a solvent can be repeated several times, if desired. The solvent from the gel can be removed by drying under normal pressure or in vacuum at room or elevated temperature. The thusly dehydrated gel, when put into a drug solution, reswells to the initial swelling ratio. We have found this method to be very convenient for loading cross-linked gels with a drug.

When a drug delivery system with drug molecules covalently attached to polymers forming a gel is desired, the drug can be directly introduced into the reaction mixture during gel preparation. Essentially the same reaction conditions can be used. The suitable drug substances are those which contain chemical groups reactive towards the cross-linking agent, preferably, divinyl sulfone. Examples of such chemical groups are hydroxyl, amino and sulfhydryl groups. An example of the drug which can be used in this process is the antibiotic gentamicin.

DETAILED DESCRIPTION OF THE INVENTION

Example 1

This example illustrates the drug delivery capability of hyaluronic acid solutions. Fluorescein was used as a model substance to visualize the effect of hylan on tear film breakup times (B.U.T.).

An 0.1% solution of sodium hyaluronate obtained from rooster combs in 0.15M aqueous sodium chloride was prepared.

Dry sodium fluorescein was added to this solution so that the final concentration of fluorescein was 0.125%. A solution of 0.125% sodium fluorescein in a balanced salt solution was used as a control.

Aotus trivargotus monkeys (2) were anesthetized and maintained on ketamine (12.5 mg/kg) and rompun (2 mg/kg) by intramuscular injection. Once anesthetized each monkey was immobilized. The eyelids of the eye were held open for topical instillation of one 10 $\mu$l drop of balanced salt solution (BSS) containing 0.125% sodium fluorescein. The lids were manually blinked twice to distribute the dye and then left open for a control measurement. A stopwatch was begun immediately after the second blink. The eye tear film was scanned with a broad beam slit in a darkened room using a blue filter (Nikon slit lamp) until the film began to break up and disappear. At this point the stopwatch was stopped and the time recorded.

After the control B.U.T. measurements were made, the same monkeys were used to test the 0.1% HA/0.125% fluorescein solution using the same technique as described for the control.

Values of tear film break-up time (B.U.T.) are listed in Table 1; SEM=standard error of the mean; BSS=balanced salt solution.

TABLE 1

| | B.U.T. (sec) | SEM |
|---|---|---|
| Control BSS/0.125% fluorescein | 33 | 11 n = 9 |
| 0.1% HA ophthalmic solution/ 0.125% fluorescein | 446 | 126 n = 6 |

The data indicates that the presence of HA in an eye solution increases the length of time the tear film covers the cornea, and therefore increases the availability of molecules combined with HA in this solution.

Example 2

This example illustrates the preparation of an hyaluronic acid putty containing salicylic acid.

A 2% solution of sodium hyaluronate was prepared in 0.2N aqueous sodium hydroxide. 1.38 g. (0.01M) of salicylic acid were stirred into 50 ml of the above solution and 2.5 ml of 4N aqueous sodium hydroxide were added to the mixture to neutralize the alkali and a slight excess of the acid (about 0.2 ml) was subsequently used to bring the pH of the mixture to about 2.5.

The product obtained consisted of a very elastic hyaluronic acid putty in which finely dispersed salicylic acid was evenly distributed. This formulation can be spread as a thin layer on the skin and used for slow delivery of salicylic acid to the skin.

Example 3

This example illustrates the slow release of radioactively labeled serotonin(N-hydroxytryptamine binoxolate, 5-[1,2 - $^3$H(N)]-) from hyaluronic acid solution.

An 0.1% solution of sodium hyaluronate obtained from rooster combs in water was prepared and mixed with $^3$H-serotonin (1 $\mu$Ci/ml; final concentration of $^3$H-serotonin=40nM). 5 ml of the $^3$H-serotonin/0.1% sodium hyaluronate solution were placed in dialysis tubing (10,000MW cutoff) and then placed into a beaker containing 500 ml of distilled water. A 5 ml solution of 40 nM $^3$H-serotonin in water was placed into dialysis against 500 ml distilled water in a second beaker. Triplicate 0.05 ml aliquots were removed from each beaker at regular time intervals up to 3 hours; one 24 hour aliquot was made and the contents of the dialysis bags were analyzed.

For the mixture of 0.1% sodium hyaluronate and labeled drug, the rates of release ($\mu$Ci/hour/ml) and the % of release were: 0.108 (10 minutes) and 2.3%; 0.096 (60 minutes) and 14.6%; 0.084 (120 minutes) and 27%; the average rate of release over 3 hours was 0.098±0.032 with 33.7% of the drug released; there was 20% (0.78 $\mu$Ci) of added drug remaining in the HA solution after 24 hours.

For the water solution of labeled drug the rates of release ($\mu$Ci/hr/ml) and % release were: 3.42 (10 minutes) and 14.3%; 0.204 (60 minutes) and 47.7%; 0.16 (120 minutes) and 70.4%; the average rate of release over 3 hours was 0.308±0.192 with 82.2% of the drug released. At 24 hours 2% of the drug remained inside the dialysis bag (98% release).

The results indicate that the presence of HA in a mixture of this drug reduces the rate of release by approximately 10 fold.

Example 4

This example illustrates the obtaining of a cross-linked hyaluronic acid gel in particulate form.

0.3410 g. of sodium hyaluronate obtained from rooster combs (instrinsic viscosity in 0.15M solution of NaCl [$\eta$] 3850,MW about 2.5×10$^6$) was mixed with 8.1840 g. of 0.2M NaOH solution to give a 4% by weight solution after stirring for 30 minutes. Then 0.0721 g. of divinyl sulfone was stirred into the solution. The weight ratio HA/DVS was about 4.7. A strong gel formed in about 15 minutes. The gel was left for one hour and then put into one liter of distilled water. The gel was left to swell in water overnight. Then it was broken into small particles by vigorous stirring in water. The gel particles were filtered off and washed several times with water. Colorless, water clear particles were obtained. To determine the swelling ratio of the gel, a sample weighing about 1 g. was centrifuged in a glass filter at 3,000 rpm for 2 hours. Then the particles left on the filter were hydrolyzed with 2 ml of 1N H$_2$SO$_4$ solution for 3 hours at 95°-98° C. The clear solution obtained was neutralized upon cooling with 2 ml of 1N NaOH solution and the glucuronic acid content was determined by the carbazole method (An Automated Method for the Determination of Hexuronic Acids, Analytical Biochemistry, 2, 517-558 [1965]). The HA content in the starting gel was calculated and the swelling ratio was expressed as 100/[HA]% where [HA]% is a percent of HA in the swollen gel.

The swelling ratio in water of the gel obtained was 820.

Example 5

This example illustrates the loading of hyaluronic acid gel particles with a physiologically active substance by diffusion and slow release of this substance from the product.

In this experiment, a radioactive labeled substance, hydroxytryptamine binoxolate, 5-[1,2-$^3$H(N)]-, was used. 5 $\mu$l of a 40 $\mu$M solution of the substance was mixed with 5 ml of cross-linked HA gel particles obtained according th Example 4 and the mixture was kept for 4 hours. Then the mixture was put into dialysis tubes and dialyzed against 0.15M NaCl solution for 24 hours. For the mixture of the labeled substance and the cross-linked gel, 54% of the starting amount of the labeled material was left in the dialysis tube, whereas only 10% remained for the water solution of the same substance used as a control. This demonstrates that the cross-linked gel of HA slows down the release of the low molecular weight substance by a factor of more than 5 times.

Example 6

This example illustrates the loading of hyaluronic acid gel particles with a physiologically active substance by dehydration of the gel and slow release of this substance from the product.

The hyaluronic acid gel particles obtained according to Example 4 were used. 50 ml of the gel were mixed with 100 ml of ethyl alcohol and the mixture was kept for 6 hours. Then, the contracted gel particles were separated by filtration and mixed with 50 ml of ethyl alcohol and left for 4 hours. The particles were separated and dried in vacuum at room temperature (about 20° C.) for 1 hour. The dry particles were mixed with 50 ml of 40 nM solution of $^3$H-serotonin (1 $\mu$Ci/ml) in water and left for 24 hours at 4° C. The volume of reswollen gel particles was 50 ml. 2.5 ml of the gel particle/labeled drug mixture was placed into dialysis against 500 ml of water. A mixture of 40 nM labeled serotonin in water was prepared and placed into dialysis against 500 ml of water in a second beaker.

Aliquots from the beaker were made at regular intervals and the radioactivity measured in order to determine the amount of drug delivered over a 48 hour period.

For the mixture of gel particle/labeled drug the percent release of the drug at 1, 24 and 48 hours was 33%, 65% and 93% while the aqueous solution of labeled drug delivered 95% of the drug after only 4 hours. These results demonstrate the ability of HA gel particles to dramatically reduce the rate of release of this drug into an aqueous medium.

Example 7

This example illustrates the preparation of a hyaluronic acid gel membrane containing the antibiotic gentamicin and the delivery of this drug from the membrane.

1.60 g. of air-dried sodium hyaluronate (water content about 15 wt. %) obtained from rooster combs (limiting viscosity number 4580 cc/g.) was dissolved in 48 ml of 0.2N sodium hydroxide for about 1 hour. 0.29 g. of divinyl sulfone was added to 5 ml of 0.2N sodium hydroxide and the resulting solution was stirred into the sodium hyaluronate solution. After about 2 minutes of stirring, the reaction mixture, which was still liquid, was poured onto a glass plate as a layer of about 1 mm thickness and left for about an hour. A strong resilient gel film was formed which was dehydrated by placing it first in isopropanol—water (4/1 mixture) for 45 minutes, then in pure isopropanol for 30 minutes. The dehydrated film was dried first in air for 30 minutes and then in vacuum for 30 minutes at room temperature. The dry, milky-white, fragile film was loaded with gentamicin by putting 1 cm$^2$ pieces of the film into 0.5 ml of a 5 mg/ml solution of gentamicin in phosphate buffered saline and incubating for 18-24 hours at 4° C.

After treatment, each 1 cm$^2$ film was rinsed with 10 ml 0.15M NaCl solution and then the pieces were placed into an antimicrobial assay system in order to determine the period of time the film maintained antimicrobial activity (length of effectiveness) against *E. Coli.*

In this assay, samples of HA membrane/gentamicin were placed on an agar (MCA) surface formed in the well of a 24 well Falcon plate (2 ml volume/well, 1.8 cm diameter). Immediately after the films were applied, 0.10 ml of a 10$^7$ dilution of a 24 hour Pennassay *Eschericia Coli* culture of bacteria were added to the agar wells. The controls were: agar well plus gentamicin solution (10 μg) and *E. Coli*, agar wells plus *E. coli* only, agar wells plus buffer and *E. Coli.*

After 24 hours at 37° C., all wells with bacteria and HA membrane/gentamicin were free of bacterial colonies; control wells (±buffer) had 10≧100 colonies, wells containing gentamicin and *E. Coli* were free of bacteria.

These same HA/gentamicin films were then transferred to fresh agar wells and a fresh inoculum of bacteria was added. Controls were the same as described above. After 24 hours each well was examined for bacterial growth. If there was zero bacterial growth, the HA/gentamicin film was transferred to a fresh well at each 24 hour interval.

In these experiments the HA membrane/gentamicin samples prevented bacterial growth for 3 full days (3 transfers) indicating that the HA membrane was slowly releasing significant, biologically effective quantities of this antibiotic over a period of 3 days.

Example 8

This example illustrates the preparation of a mixed gel membrane containing hyaluronic acid and chondroitin sulfate and loaded with gentamicin as well as illustrating the delivery of the drug from this membrane.

About 1.0 g. of sodium hyaluronate obtained from rooster combs (limiting viscosity number 3100 cc/g.) was dissolved in 40 ml of 0.2N sodium hydroxide for about 45 minutes and about 1.0 g. of chondroitin sulfate (Sigma Co., mixed isomers, grade III) was dissolved in the resulting solution by additional stirring for about 15 minutes. Then, a solution of 0.35 g. of divinyl sulfone in 9.0 ml of 0.2N sodium hydroxide was stirred into the polymer solution for about 5 minutes. The reaction mixture, which was still liquid, was cast as 1 mm thick layer onto a glass plate and left for an hour. The strong gel film obtained thereby was first kept in isopropanol for 30 minutes, then in a fresh change of isopropanol for another 30 minutes. The dehydrated film was dried in air for bout 8 hours and for 3 hours in vacuum at 50° C. The dry, milky-white film that was obtained was cut into 1 cm$^2$ pieces put into 1 ml of a solution of gentamicin (1 mg/ml) containing 0.1% $^{125}$I-gentamicin for 18-24 hours at 40° C. After treatment it was rinsed with 10 ml of 0.15M NaCl solution and then placed into a beaker of 10 ml of 0.15M NaCl. 10 μl aliquots were removed at intervals and the radioactivity ($^{125}$I) measured in a gamma counter. After 24 hours at room temperature, the 1 cm$^2$ HA/CS membrane/gentamicin released 71% of the gentamicin originally taken up; after 72 hours, 83% had been released. Approximately 17% (1.65) of the gentamicin remained associated with the HA/CS membrane. These results indicate that this antibiotic may be delivered at a slow rate from a hyaluronic acid-chondroitin sulfate membrane.

Example 9

This example illustrates a cross-linked hyaluronic acid gel with gentamicin covalently attached to the polymer and delivery of the drug from the gel.

0.52 g. of sodium hyaluronate was dissolved in 19.4 ml of 0.2N sodium hydroxide for about an hour and 0.52 g. of gentamicin sulfate was stirred into the solution followed by adding 1.0 ml of 4N sodium hydroxide to increase the pH of the mixture. To the uniform solution thereby obtained, a solution of 0.23 g. of divinyl sulfone in 1.0 ml of 0.2N sodium hydroxide was added and the mixture was stirred for about 5 minutes. The still liquid mixture was cast onto a glass plate as a flim of 1 mm thickness and left for 1 hour. The gel film obtained was treated in isopropanol-water 9/1 mixture for 30 minutes, then in pure isopropanol for 30 minutes, then dried in air for 30 minutes, and finally, in vacuum at room temperature for 60 minutes. The dry, milky-white film obtained was placed into 50 ml of 0.15 ml NaCl solution and incubated for 24 hours at 4° C.; the 50 ml wash solution was replaced with a second 50 ml of saline, and incubated an additional 24 hours. This was repeated once more.

1 cm$^2$ pieces of the gentamicin-hyaluronic acid then were placed in a 1.8 cm agar well with an inoculum of *E. Coli* (0.1 ml of a 10$^7$ dilution of a 24 hour Pennassay culture). After 24 hours at 37° C. there was 75% inhibition of *E. Coli* colony formation; the film was transferred to a fresh agar well with bacteria at each 24 hour time period (up to 4 days; experiment was not carried out any longer). At 48 and 72 hours there was 95% inhibition of bacterial growth. These results indicate that the gentamicin covalently attached to a cross-linked hyaluronic acid gel remained biologically active for 4 days at 37° C.

Example 10

This example illustrates the preparation of a soft hyaluronic acid gel loaded with mydriacyl and the delivery of the drug in an ophthalmic application.

0.58 g. of sodium hyaluronate obtained from rooster combs (limiting viscosity number 4500 cc/g.) was mixed with 20 ml of water and allowed to swell for about 20 hours. Then 2 ml of 2N sodium hydroxide were added to the mixture which turned into a uniform solution after about 10 minutes of stirring. 0.10 g. of divinyl sulfone was dissolved in 2.4 ml of water and stirred into the above solution. The mixture was left for 70 minutes and the gel obtained was put into 223 ml of Biotrics buffer (0.15M sodium chloride solution buffered with phosphates to pH about 7.2). The gel was left to swell for 3 hours and 1 ml of 2N hydrochloric acid was added to the mixture. After 1 hour 0.6 ml of 2N hydrochloric acid was added and the mixture was left for 16 hours. 0.35 ml of 2N hydrochloric acid was added and the swollen gel was slowly stirred for 3 days in the buffer. A uniform viscoelastic soft gel was obtained which was dialyzed against 0.15M sodium chloride for 5 days. The concentration of the cross-linked hyaluronic acid in the gel was 0.21%. This gel was mixed with 1% mydriacyl (tropicamide) in balanced salt solution to produce a final concentration of 0.5%. 0.5% mydriacyl in a balanced salt solution was used as a control. A balanced salt solution without the drug was used as a negative control.

New Zealand white rabbits (12) were placed in a restrainer and baseline pupil diameters were measured using an American Optical slit lamp equipped with a micrometer. 50 $\mu$l of each test sample was instilled in one eye and 50 $\mu$l of the control solution was instilled in the other eye. Pupil size was measured at regular intervals for up to 450 minutes. The average increase in pupil diameter was 3.2 mm$\pm$0.80 (n=12). The rabbits which received mydriacyl solution maintained greater than 50% of this value for up to 160 minutes after which time there was a rapid decrease in pupil size, returning to normal in approximately 240 minutes.

In the rabbits which received mydriacyl in hyaluronic acid jelly, greater than 50% of the pupil size increase was maintained for an average of 340 minutes after which time there was a much slower rate of decrease in pupil size as compared to the rate of decrease observed in the rabbit eye which received mydriacyl solution without HA jelly.

These results indicate that the combination of a drug with a hyaluronic acid gel significantly prolongs the period of effectiveness of the drug when applied topically to the surface of the eye.

Example 11

This example illustrates the preparation of hyaluronic acid immobilized in a porous polymeric sponge and delivery of a drug from this product.

0.32 g. of sodium hyaluronate obtained from rooster combs (limiting viscosity number 4900 cc/g.) was dissolved in 13 ml of 0.2N sodium hydroxide to give 2.5 wt. % solution. A solution of 0.08 g. of divinyl sulfone in 1 ml of 0.2N sodium hydroxide was added and the mixture was stirred vigorously for about 5 minutes. Cylindrical porous sponges made of a polyurethane were dipped into the still liquid reaction mixture, squeezed in the mixture several times to remove air from the pores and left in the mixture for 5 minutes. Then the sponges were removed from the mixture and left for an hour to allow the reaction mixture to gel inside the pores. Then, the sponges with gel filling the pores were put into 0.15M aqueous sodium chloride and kept there for 24 hours. Finally, the sponges were dried in air for 30 hours. The thusly obtained dry sponges were incubated in 5 ml of 40 nM $^3$H-serotonin (1 $\mu$Ci/ml) for 24 hours at 40° C. After this time each sponge was dipped 3 times into 10 ml of H$_2$O and then each placed into a beaker containing 50 ml of distilled water. Triplicate 0.05 ml of aliquots of water medium were removed at regular intervals up to 96 hours and the radioactivity measured in a liquid scintillation counter. The % release of the labeled drug was determined from the total uptake.

For the sponge with immobilized hyaluronic acid gel the % release of drug at 0.5, 1, 4, 72 and 96 hours was: 3.8%, 4.9%, 8.8%, 53% and 62%, respectively. The average rate of release was 2.03%/hr/sponge$\pm$1.18%.

For the control (untreated sponge), the % release of drug at 0.5, 1, 4, 72 and 96 hours was: 38.7%, 45.1%, 54%, 92% and 92%, respectively The average rate of release was 26.8%/hr/sponge$\pm$40.8%.

The results clearly indicate that the immobilized HA gel causes a 20 fold decrease in the average rate of release of the labeled drug and also reduces the variability in the rate of release of the drug from the sponge.

Example 12

This example illustrates the preparation of a cotton gauze with a hyaluronic acid gel film immobilized on it and delivery of a drug from this system.

A 0.2% wt. % solution of sodium hyaluronate obtained from rooster combs (limiting viscosity number 4900 cc/g.) in water-isopropanol mixture 90/10 was prepared. Pieces of bleached cotton gauze were dipped in the solution and then dried in air for 2 hours. The procedure was repeated one more time. The gauze with a polymer film on it was dipped in a mixture of the following composition, percent by weight: acetone 70, water 30, 0.2N sodium hydroxide 4, divinyl sulfone 1.6, and kept in this mixture for 30 minutes. Then the gauze was removed from the solution, dried in air for 60 minutes and put in water to remove alkali and other soluble substances and to allow the cross-linked hyaluronic acid coating to swell. The thusly prepared gauze was air dried and cut into 1 cm$^2$ pieces. Each sample was placed in a solution of gentamicin/$^{125}$I-gentamicin; the final gentamicin concentration was 1 mg/ml. After incubation for 18-24 hours at 4° C., each 1 cm$^2$ piece was rinsed in 10 ml of 0.15 ml NaCl and placed in 20 ml of 0.15M NaCl. 0.1 ml aliquots of medium were removed at 1, 2, 4, 24, 48 and 96 hours.

The HA/gauze sample releases 6.3% and 11.4% of the imbibed gentamicin within 24 and 96 hours. The control gauze sample released 11.2 and 20% at these same time intervals. These results indicate that by immobilizing hyaluronic acid on a cotton gauze, the rate of release of a drug such as the antibiotic gentamicin may be reduced considerably (i.e., about 50%).

We claim:

1. A drug delivery system comprising a polymeric component which is an insoluble hyaluronan or a soluble hylan and a selected amount of at least one substance having biological or pharmacological activity and which is controllably releasable from said system so as to effect delivery of a therapeutically effective amount of said substance to a desired site.

2. A drug delivery system in accordance with claim 1 wherein the polymeric component is a soluble hylan and comprises an aqueous hylan solution.

3. A drug delivery system in accordance with claim 2 wherein the substance is dissolved or dispersed in the aqueous solution.

4. A drug delivery system in accordance with claim 2 wherein the solution is a viscoelastic putty.

5. A drug delivery system in accordance with claim 2 wherein the hylan concentration is about 0.05 to 4% by weight.

6. A drug delivery system in accordance with claim 2 in the form of an injectable product.

7. A drug delivery system in accordance with claim 2 in the form of a topical product.

8. A drug delivery system in accordance with claim 7 and comprising eye drops.

9. A drug delivery system in accordance with claim 7 wherein the hylan has a molecular weight of at least about $1 \times 10^6$ and the concentration of hylan is from about 0.05 to 2% by weight.

10. A drug delivery system in accordance with claim 2 wherein the substance is serotonin.

11. A drug delivery system in accordance with claim 4 wherein the substance is salicylic acid.

12. A method of obtaining a product in accordance with claim 2 comprising dissolving or dispersing the substance in a water or saline solution of hylan.

13. A method of obtaining a product in accordance with claim 2 comprising mixing a solution or dispersion of the substance with a hylan solution.

14. A method of obtaining a product in accordance with claim 4 comprising adding the substance to a solution of hylan and adjusting the pH of the resulting mixture to about 2.5.

15. A drug delivery system in accordance with claim 1 wherein the polymeric component is an insoluble hyaluronan.

16. A drug delivery system in accordance with claim 15 wherein the insoluble hyaluronan is a cross-linked gel of hyaluronan or a cross-linked gel of hyaluronan and at least one other hydrophilic polymer.

17. A drug delivery system in accordance with claim 16 wherein the other hydrophilic polymer is any such polymer having a functional group capable of reacting with divinyl sulfone.

18. A drug delivery system in accordance with claim 17 wherein the other hydrophilic polymer is a natural or synthetic polysaccharide selected from the group consisting of hydroxyethyl cellulose, carboxymethyl cellulose, xanthan gum, glycosaminoglycans, a protein or glycoprotein selected from the group consisting of collagen, elastin, albumin, a globulin, keratin sulfate, a sulfated aminoglycosaminoglycan and a synthetic water soluble polymer, selected from the group consisting of polyvinyl alcohol and its co-polymers and co-polymers of poly-(hydroxyethyl)methacrylate.

19. A drug delivery system in accordance with claim 16 wherein the insoluble hyaluronan is in the form of a molecular cage and the substance is dispersed within said molecular cage.

20. A drug delivery system in accordance with claim 16 wherein the substance is covalently bonded to the macromolecules of hyaluronan or said at least one other hydrophilic polymer.

21. A drug delivery system in accordance with claim 19 in combination with a support or substrate therefor.

22. The combination in accordance with claim 21 wherein the support or substrate is a polymeric porous sponge, a gauze or a polymeric film.

23. A method of obtaining a product in accordance with claim 16 comprising placing the gel into a solution of the substance and allowing the substance to diffuse into the gel whereby a product having the substance uniformly dispersed therethrough is obtained.

24. A method of obtaining a product in accordance with claim 16 comprising dehydrating the gel and placing the dehydrated gel into a solution of the substance to cause reswelling of the dehydrated gel, said substance being diffused into the gel while the reswelling occurs.

25. A method in accordance with claim 24 wherein dehydrating is effected by treating the gel with a water miscible solvent or by drying.

26. A method in accordance with claim 25 wherein a water miscible solvent is used.

27. A method in accordance with claim 26 wherein the water miscible solvent is ethanol, isopropanol or acetone.

28. A method of obtaining a product in accordance with claim 16 comprising placing a concentrated gel in a solution of said substance and allowing the gel to swell in said solution whereby the substance is diffused into the gel while it is swelling.

29. A drug delivery ststem in accordance with claim 16 wherein when the insoluble hyaluronan is a cross-linked hyaluronan gel and at least one other hydrophilic polymer, the hyaluronan comprises from 5 to 95% by weight of said insoluble hyaluronan.

30. A method of obtaining a product in accordance with claim 20 which comprises subjecting hyaluronan or a mixture of hyaluronan and the other hydrophilic polymer to a cross-linking reaction in the presence of said substance provided that said substance has a chemical group reactive toward the cross-linking agent to thereby cause the formation of covalent bonds between said chemical group and the hyaluronan or the other hydrophilic polymer.

31. A method in accordance with claim 30 wherein the chemical group is hydroxyl, amino or sulfhydryl.

32. A method in accordance with claim 30 wherein said substance is gentamicin.

33. A drug delivery system in accordance with claim 21 and comprising a membrane formed of a gel of hyaluronan containing gentamicin.

34. A drug delivery system in accordance with claim 21 and comprising a membrane formed of a gel of hyaluronan and chondroitin sulfate containing gentamicin.

35. A drug delivery system in accordance with claim 20 and comprising a gel of cross-linked hyaluronan and gentamicin covalently attached thereto.

36. A drug delivery system in accordance with claim 21 and comprising a gel of hyaluronan containing mydriacyl.

37. A drug delivery system in accordance with claim 21 and comprising a porous polymeric sponge, said sponge having a hyaluronan gel immobilized therein together with said substance.

38. A drug delivery system in accordance with claim 37 wherein said substance is serotonin.

39. A drug delivery system in accordance with claim 37 wherein said sponge is formed of a polyurethane.

40. A drug delivery system in accordance with claim 21 and comprising a cotton gauze, said gauze having a hyaluronan gel immobilized therein together with said substance.

41. A drug delivery system in accordance with claim 40 wherein said substance is gentamicin.

* * * * *